(12) United States Patent
Baars et al.

(10) Patent No.: US 9,192,557 B2
(45) Date of Patent: Nov. 24, 2015

(54) WATER-FREE COSMETIC PREPARATION

(75) Inventors: Beatrice Baars, Nuremberg (DE);
Manfred Bugla, Forchheim (DE);
Kerstin Loetzerich-Bernhard,
Neunkirchen a. Br. (DE)

(73) Assignee: Schwan-STABILO Cosmetics GmbH & Co. KG, Heroldsberg (DE)

( * ) Notice: Subject to any disclaimer, the term of this patent is extended or adjusted under 35 U.S.C. 154(b) by 2267 days.

(21) Appl. No.: 11/628,558

(22) PCT Filed: Jul. 10, 2006

(86) PCT No.: PCT/EP2006/006735
§ 371 (c)(1),
(2), (4) Date: Nov. 30, 2006

(87) PCT Pub. No.: WO2007/006536
PCT Pub. Date: Jan. 18, 2007

(65) Prior Publication Data
US 2008/0292668 A1    Nov. 27, 2008

(30) Foreign Application Priority Data

Jul. 8, 2005 (DE) .................... 20 2005 010 761 U
Dec. 2, 2005 (DE) ........................ 10 2005 057 593

(51) Int. Cl.
| | | |
|---|---|---|
| A61K 8/02 | (2006.01) | |
| A61K 8/44 | (2006.01) | |
| A61K 8/29 | (2006.01) | |
| A61K 8/365 | (2006.01) | |
| A61K 8/55 | (2006.01) | |
| A61K 8/67 | (2006.01) | |
| A61K 8/68 | (2006.01) | |
| A61K 8/73 | (2006.01) | |
| A61K 8/92 | (2006.01) | |
| A61K 8/97 | (2006.01) | |
| A61Q 19/00 | (2006.01) | |
| A61Q 19/08 | (2006.01) | |
| A61Q 1/04 | (2006.01) | |
| A61Q 1/06 | (2006.01) | |
| A61Q 1/10 | (2006.01) | |
| A61Q 17/04 | (2006.01) | |

(52) U.S. Cl.
CPC ............... *A61K 8/44* (2013.01); *A61K 8/0229* (2013.01); *A61K 8/29* (2013.01); *A61K 8/365* (2013.01); *A61K 8/55* (2013.01); *A61K 8/675* (2013.01); *A61K 8/678* (2013.01); *A61K 8/68* (2013.01); *A61K 8/735* (2013.01); *A61K 8/922* (2013.01); *A61K 8/97* (2013.01); *A61Q 19/00* (2013.01); *A61Q 19/08* (2013.01); *A61K 2800/872* (2013.01); *A61Q 1/04* (2013.01); *A61Q 1/06* (2013.01); *A61Q 1/10* (2013.01); *A61Q 17/04* (2013.01)

(58) Field of Classification Search
None
See application file for complete search history.

(56) References Cited

U.S. PATENT DOCUMENTS

| | | | | |
|---|---|---|---|---|
| 4,382,961 | A  * | 5/1983 | Nedeczky et al. | 424/401 |
| 5,665,778 | A    | 9/1997 | Semeria et al. | |
| 5,667,770 | A    | 9/1997 | Szweda et al. | |
| 6,528,071 | B2   | 3/2003 | Vatter et al. | |
| 6,649,151 | B2 * | 11/2003 | Barone et al. | 424/64 |
| 6,790,451 | B2 * | 9/2004 | Nakanishi | 424/401 |
| RE38,623 | E  * | 10/2004 | Hernandez et al. | 424/59 |
| 2004/0005282 | A1* | 1/2004 | Gaetani et al. | 424/63 |
| 2006/0165645 | A1* | 7/2006 | Lebok et al. | 424/74 |

FOREIGN PATENT DOCUMENTS

| | | | | |
|---|---|---|---|---|
| DE | 2038748 | * | 8/2003 | ............. A61K 8/19 |
| EP | 0370470 A2 | * | 5/1990 | ............. A61K 7/13 |
| EP | 1 110 971 | | 6/2001 | |
| EP | 1 352 640 | | 10/2003 | |
| WO | WO 2004/024105 | * | 3/2004 | ............. A61K 7/021 |

OTHER PUBLICATIONS

Lapinskas (Echium, 2002) and attached Internet Archive Report).*
Murad et al (Wrinkle Free Forever, pp. 96-97, 2004).*
Michalun et al () .*
Gore (Eating for Successful Fat Loss, p. 25, 1999).*
RD443030A, Feb. 2001, Anon.*
Babel et al (New Trends and Developments in Biochemical Engineering, p. 156, 2004).*
Fulmer et al (J Invest Dermatol 86:598-602, 1986).*
Long et al (Arch Dermatol Res 277:284-287, 1985).*
Spiclin et al (Int J Pharmaceut 256:65-73, 2003).*
Elsner et al (Cosmetics, p. 292, 2000).*
Williams (Townsend Lett for Doctors and Patients, 2004).*
Emsley (Vanity, Vitality, and Virility, p. 15, 2004).*
Derwent Accession No. 2001-449461.*
Derwent Accession No. 2004-000775.*
www.seatons-uk.co.uk (online as of Apr. 29, 2005 as evidenced by the attached Internet Archive Report).*
Darmstadt et al (Acta Paediatr 91:546-554, 2002).*

* cited by examiner

*Primary Examiner* — Craig Ricci
(74) *Attorney, Agent, or Firm* — Bachman & LaPointe, P.C.

(57) ABSTRACT

A water-free composition, in particular a cosmetic composition, in the form of a pencil with a cast or extruded lead or a workable paste which is suitable for cosmetic uses, in particular in the field of decorative cosmetics, for coloring, improving the appearance of and caring for keratinic materials such as for example the skin, semi-mucous membranes and mucous membranes, eyelashes, eyebrows and the hair. That preparation includes a specifically matched combination of water-soluble and lipid-soluble active substances in the form of a so-called "active substance cocktail". The production and use of that composition are also described.

37 Claims, No Drawings

WATER-FREE COSMETIC PREPARATION

BACKGROUND OF THE INVENTION

The invention concerns a water-free cosmetic preparation. The preparation can be in the form of a lead for use in a pencil or a workable paste, which is suitable for cosmetic uses, in particular in the field of decorative cosmetics, for coloring, improving the appearance of and caring for keratinic materials such as for example the skin, semi-mucous membranes and mucous membranes, the lips, the eyelids, the eyelashes and eyebrows and the surrounding area. By way of example mention may be made here of lipstick, lip rouge, blusher, lipliner, eyeliner, eyebrow pencils, kohl, kajal, makeup, effect party makeup, hair coloring pencil, mascara, hair mascara, masking pencil, concealer or eyeshadow.

It can also be used as a lip care pencil, lip balm, lip gloss, a fixing foundation for the lips, a care foundation for care of the skin or as a sun protection agent. Preferably the preparation according to the invention, in particular a cosmetic preparation, contains a combination of water-soluble, in particular easily water-soluble and lipid-soluble active substances which can be present in the form of an active substance complex which is especially adapted in respect of its action, referred to as an "active substance cocktail". In this respect the expression "easily water-soluble" is used to denote those active substances of which at least 10 g per 100 g of water can be dissolved at ambient temperature—that is to say at 23+/−2° C.-. The preparation and in particular the cosmetic preparation is preferably present in water-free form.

A human being naturally has an inherent wish to appear beautiful or handsome and attractive and to interact with fellow human beings in as well-groomed and vital fashion as possible. Admittedly, as times pass, the ideal of beauty has undergone many different changes and the most widely varying fashion trends, but the aim of human beings was always to get as close as possible to a flawless ideal image. Therefore, besides clothing and decoration appearance and the state of the skin and the skin appendages played an essential part. In ancient times, as is known from early Egyptian wall paintings and from tomb excavations, it was important for human beings—and in particular the female gender—to optimize their external appearance by means of creative color designs. In the past a higher level of significance was evidently attributed to the color effect—if we believe the analyses of old finds—than compatibility and the presentday toxicological considerations—true indeed to the motto: "who wishes to be attractive must suffer". National and international legal regulations however have in recent times eliminated ingredients of such preparations, which were recognized as being dangerous to the consumer.

Preparations of the specified kind usually contain lipids such as for example fats or greases, oils, oil-soluble plant extracts, saturated straight and/or branched-chain alcohols with chain lengths of between $C_3$ and $C_{40}$, saturated straight and/or branched-chain medium- to long-chain fatty acids with chain lengths of between $C_6$ and $C_{40}$ or those with at least one double bond whose esters and waxes which can be of vegetable or animal origin derive from mineral sources such as for example petroleum or were obtained by synthesis or chemical modification of the specified substances. It is also known to use silicon-organic compounds such as for example dimethicone, phenyl trimethicone, diphenyl dimethicone, volatile cyclomethicones, silicone waxes, silicone resins such as for example trimethyl siloxysilicate, a frequently used film-forming agent in what are referred to as "non-transfer" preparations and the like and/or mixtures thereof.

The preparation can additionally contain a solid phase or solids phase which comprises finely divided fillers and coloring agents or mixtures thereof. In the case of sun protection agents, it is possible to use in particular finely divided pigments, so-called nanopigments of an average particle size of between 5 and 25 nm, which have a transparent action on the skin and no longer color it. Mention may be made here by way of example of silicon dioxide, titanium dioxide and zinc oxide.

It is also known to add to preparations, in particular cosmetic preparations of the specified kind, active substances which can exert positive topical actions or to which such an action is at least attributed. In accordance with the statutory requirements relating to cosmetics the action of active substances of that kind must be admittedly scientifically demonstrable, but on the other hand they may not be predominantly intended to heal or alleviate diseased states as then they would be subjected to the provisions of drug laws. The man skilled in the relevant art therefore treads a clearly very narrow dividing line and is required in that respect to research very intensively for active substances which are suitable for his purpose, and to draw a distinction from substances which are predominantly effective in terms of medical matters.

In production and processing of preferably water-free and lipid-bearing preparations of the specified kind, it is to be borne in mind that they can be exposed to elevated temperatures in the region around between 70 and 110° C. over prolonged periods of time—on the one hand when the raw materials are melted down and homogenized together with coloring agents and other additives and on the other hand when they are being put into their definitive form. In that respect the raw materials used are not to undergo chemical change, or are to undergo only a very slight chemical change, due to the action of heat and oxygen in the air. Raw substances of vegetable or animal origin, particularly when they include double bonds or conjugate double bonds in the carbon chain, have a tendency to experience rearrangement phenomena, additions, peroxide formation and the like, which can lead to adverse changes in terms of odor. Such changes can be induced or even accelerated in the manner of a catalyst action by the presence of certain pigments, in which respect mention may be made here by way of example of Manganese Violet (C I No 77742).

In general therefore cosmetic preparations are preferably produced in emulsion form, in particular if they contain water-soluble ingredients. It is then usual for the water-soluble ingredients to be dissolved in the aqueous phase and the lipid-soluble ingredients in the lipid phase and then for a stable emulsion to be produced from the two phases, possibly using emulsifiers, stabilizers and so forth. Aqueous systems generally require a preserving agent.

Now an object of the invention was to provide a preparation which contains active substances or an active substance system, wherein the active substance system comprise water-soluble and/or lipid-soluble active substances and wherein the preparation is stable, is easy to apply, adheres to the location of application and can possibly liberate the active substances contained therein at least in part with a delay.

A further object of the invention was to provide a water-free and lipid-bearing preparation which is in the form of a lead to be used in a pencil or a workable paste, which is suitable for cosmetic uses, in particular in the field of decorative cosmetics, for coloring and improving the appearance of keratinic materials such as for example the skin, semi-mucous membranes and mucous membranes, the lips and the eyelids and the surrounding area, which can be easily applied, which has good lasting adhesion and which does not migrate or migrates only to a minimal extent from the original application location into the immediate surroundings. If the preparation is in pencil form, it is to be stable in respect of storage at different storage temperatures which can arise on the varying transportation routes and at the user himself and it is not to detrimentally change in terms of the properties of use and also—if it is in the form of a workable paste—it is not to exhibit any syneresis effects after prolonged storage and is also not to experience adverse reorganization in regard to the properties of use in the sense of changes in viscosity. In addition the invention aims to provide that this preparation can be applied in soft and workable fashion, it does not become tight on keratinic materials such as for example the skin, the semi-mucous membranes and mucous membranes, the lips and the lids, and does not dry them out, it has good durable adhesion, as far as possible it does not transfer onto articles and textiles or other regions of the skin and in the immediate proximity of the eye it does not lead to irritation or other adverse sensations.

A further object of the invention was to provide the above-mentioned preparation at the same time with a selected active substance combination which is properly suited in a balanced fashion in the intended effect, in the form of an "active substance cocktail", and further to supplement it in respect of its action by cleverly selected lipidic vegetable ingredients. Finally the invention seeks to provide a preparation of the specified kind which, besides decorative properties, has excellent care effects in the sense of an ongoing vitalizing, energy-providing effect of stimulating the micro-circulation and thus the skin substance transport effect. Those actions are intended finally to positively influence the overall image of the skin, improve the fine structure of the skin surface, reduce wrinkle depth and counteract fatigue phenomena and premature skin ageing. In modern linguistic usage those intended effects are also referred to as "vitalizing", "energizing", "anti-wrinkle" and "anti-age".

SUMMARY OF THE INVENTION

The foregoing objects are attained with a water-free preparation for application to the skin containing a lipid phase with a solid phase distributed therein and an active substance system, wherein the active substance system is a combination of water-soluble and lipid-soluble active substances, wherein the water-soluble active substances are contained in the solid phase while the lipid-soluble active substances are present dissolved in the lipid phase.

DETAILED DESCRIPTION

It was surprisingly found that a cosmetic preparation which is water-free and contains water-soluble materials in the form of a solid phase provides a product which is both microbiologically and also mechanical stable, which can be easily applied, which adheres to the location of application and which in addition liberates the active substances in a specifically controlled fashion, wherein delivery, in particular for the water-soluble active substances contained in the solid phase, can take place over a prolonged period of time. That is achieved by the composition according to the invention. More specifically it was found that water-soluble substances which are added to a preparation based on lipids can be stably distributed in the preparation. When such a stabilized preparation is then applied to the skin the water-soluble active substance can be delivered to the skin only when it is in dissolved form. As the surface of the skin however provides water only in a low level of concentration, the water-soluble component is only gradually dissolved and, after it has dissolved, is made available to the skin. That effect can be still further influenced by coating the active substance particles or by microencapsulation. That makes it possible to achieve metered delivery of active substances, using simple means. It was surprising that this is possible.

In accordance with the invention therefore there is provided a preparation which besides the usual ingredients contains a lipid phase with a solid phase. In addition the water-free preparation according to the invention includes an active substance system, wherein active substances which are water-soluble and active substances which are lipid-soluble supplement each other and in combination lead to highly advantageous effects. The choice of the lipid phase means that the preparation according to the invention can be produced both in the form of a workable paste which can be from very soft and viscous to highly viscous and also in the form of a lead which can be used in a pencil. Depending on the respective proportion and nature of the structuring constituents such as for example waxes and depending on the respective processing of the material obtained the product is workable to viscous, wherein the dynamic viscosity can be set in a wide range, for example between 0.5 and 100 Pa·s. Likewise the choice of appropriate structuring ingredients means that it is possible to produce a material which is present in the form of a lead after casting or also extrusion. The lead is preferably of a self-supporting nature, that is to say it can be fitted for example into a rotary or slider mechanism.

The active substance systems used can differ according to the respective location of application. Inter alia skin-smoothing, vitalizing and moisturizing active substance systems are appropriate. Active substance systems in which water-soluble and lipid-soluble active substances supplement each other are preferred.

The active substance system is preferably in the form of two phases, namely an active substance lipid phase and an active substance solid phase. The active substance lipid phase contains lipid-soluble active substances which provide positive properties for the skin. For example fat-soluble vitamins or derivatives thereof such as nicotinic acid derivatives, panthenol derivatives, tocopherols, combinations thereof and so forth can be used here. Preferred lipid-soluble vitamin derivatives are for example panthenyl triacetate, tocopheryl nicotinate or also substances stimulating collagen synthesis such as phytosphingosine derivatives. The lipid phase can also contain vegetable extracts which can exert on the skin a regenerating, soothing or wrinkle-smoothing action or an action which is advantageous in some other way.

A particularly advantageous ingredient which can provide for at least short-term wrinkle smoothing is a compound which swells by the absorption of water and thereby fills out the wrinkles. Hydrophilic hyaluronic acid or a derivative thereof is particularly suitable for that purpose. Both water-soluble hyaluronic acid derivatives and also lipid-soluble hyaluronic acid derivatives are suitable for the preparation according to the invention. Both kinds can be incorporated into the preparation according to the invention and the hyaluronic acid component swells in each case due to the absorption of water which is available on the surface of the skin. The hyaluronic acid derivative is dispersed in dried form in the lipid phase and uniformly distributed and swells only after being applied to the skin. Suitable hyaluronic acid derivatives are for example salts of hyaluronic acid such as for example the sodium salt. Another equally well suited form of hyaluronic acid is a product which is commercially available under the name hyaluronic filling spheres and which is provided in the form of microballs. The hyaluronic acid microballs can be enclosed for example by a gel-like layer comprising a palmitate, silicon compounds or other compounds in order to protect them until they come into contact with the skin.

Microparticles which are formed from other biopolymers can also satisfy the purpose of filling wrinkles by swelling up. Thus for example biopolymers obtained from plants such as hydrolyzed wheat protein can be used for that purpose. Those particles which are also commercially available in the form of "vegetal filling spheres" can also be considered in the form of a solid phase for the preparation according to the invention.

Further ingredients which supplement the action of these skin-smoothing constituents are cell-regenerating compounds such as panthenyl derivatives, ceramides which reproduce the skin lipids, for example ceramide 3 or phytosphingosines which promote and stimulate collagen synthesis.

In another embodiment of the present invention which is particularly suitable for the production of eyeliners a combination of water-soluble salts and vegetable extracts is used as the active substance system. The salts have a vitalizing action and supply the skin with important trace elements while the lipid-based extracts act as radical catchers, skin-smoothing agents and collagen synthesis-promoting agents. In that respect the salts considered are in particular alkaline earth, zinc, and copper salts of di-, tri, or polyhydroxyacids. The hydroxy groups provide that once again water is absorbed, which results in a delayed and/or more long-lasting action on the part of the active substances. Aspartate and gluconate salts have proven to be particularly suitable.

It is essential for the preparation according to the invention that there are a lipid phase and a solid phase which contain an active substance system. Further suitable ingredients of the preparation are described hereinafter.

Suitable raw materials for production of the specified preparations, as already stated, are lipids which are referred to hereinafter with the designations known to the man skilled in the relevant art in accordance with the "International Nomenclature of Cosmetic Ingredients" (referred to as the "INCI names") and which can also be present in at least partially hydrated form. By way of example mention is made here of fats and oils of vegetable, animal, mineral or synthetic origin such as for example hydrogenated jojoba oil, (hydrogenated) cottonseed oil, (hydrogenated) castor oil, (hydrogenated) vegetable oil, (hydrogenated) rapeseed oil, (hydrogenated) sesame oil, (hydrogenated) coco glycerides, (hydrogenated) palm kernel oil, (hydrogenated) olive oil, (hydrogenated) sweet almond oil, (hydrogenated) peanut oil, *Magnifera indica* (mango seed oil), *Limnanthes alba* (meadowfoam oil), *Butyrosperum parkii* (shea butter), *Macadamia ternifolia* nut oil (Macadamia nut oil), *Buxus chinensis* oil (jojoba oil), *Persea gratissima* oil (avocado oil), avocado extract (phytosterols and *Persea gratissima* oil), calendula oil, hypericum oil, (hydrogenated) stearyl olive esters, *Theobroma grandiflorum* (capuacu butter), shark liver oil, squalan, squalen, caprylic/capric triglyceride, (hydrogenated) polybutene, mineral oil, oil-soluble plant extracts and mixtures of the said substances. Of the straight-chain or branched alcohols with chain lengths of between $C_3$ and $C_{40}$, medium- to long-chain fatty acids with chain lengths of between $C_6$ and $C_{40}$ and esters thereof with a chain length of between $C_3$ and $C_{40}$ in the alcohol residue and a chain length of between $C_6$ and $C_{40}$ in the carboxylic acid residue, the following have been found to be particularly suitable, for example: octyl dodecanol, myristyl octadecanol, myristyl alcohol, cetyl alcohol, stearyl alcohol, behenyl, alcohol, melissinyl alcohol, lauric acid, myristic acid, palmitinic acid, stearic acid, isostearic acid, erucic acid, behenic acid, cerotinic acid, melissinic acid, isopropyl myristate, isopropyl palmitate, butyl stearate, hexyl oleate, myristyl lactate, myristyl myristate, myristyl isostearate, myristyl stearate, isostearyl isostearate, cetyl palmitate, behenyl crucate, behenyl behenate, behenyl stearate, behenyl isostearate, C20-40 alkyl stearate and mixtures thereof. Waxes that have proven to be particularly suitable are *copernica cerifera* (carnauba), *euphorbia cerifera* (candelilla wax), *cera alba* (beeswax), *rhus succedanea* fruit wax (Japan wax), *oryza sativa* bran wax, (rice bran wax), ouricury wax, polyglyceryl-3 beeswax (*cera bellina*), synthetic beeswax, synthetic wax, polyethylene, *cera microcristallina*, paraffin wax, waxes from Fischer-Tropsch synthesis and mixtures thereof.

The amounts of lipid components which are liquid at ambient temperature, that is to say in the range of 23+/−2° C., that is to say oils and liquid esters and wax esters, are in that case in the range of between 5 and 80% by weight, preferably in the range of between 15 and 50% by weight, while those of the lipid components which are solid at ambient temperature, in the range of 23+/−2° C., that is to say fats, fatty alcohols, fatty acids, their esters and waxes, are in the range of between 1 and 65% by weight, preferably in the range of between 5 and 45% by weight. It will be appreciated that specifying the amounts used and the amounts preferably used is with the proviso that the total of all the stated components of one of the compositions further listed hereinafter always makes up 100.000% by weight. The amounts involved in each individual case can certainly fall slightly below or also rise above the amounts specified here and also hereinafter and in that respect preparations according to the invention can nonetheless be obtained. From the point of view of the man skilled in the relevant art that would be in no way unexpected on the basis of the large number of the above-mentioned possible substances—he would therefore know that rising above or falling below the specified values in that way would not constitute a departure from the scope of the invention set forth hereinbefore.

Combining various waxes, wax esters, various oils and other lipid components makes it possible to adjust the consistency of the material obtained, as is known to the man skilled in the art. The appropriate combination can be found for the respective purpose, by a few routine tests. Thus inter alia viscosity or workability of the material can be influenced by the use of waxes with different melting points and by using different proportions of oil and wax.

A further constituent which is essential to the invention is a solid phase which comprises finely divided fillers and at least one coloring agent or a mixture of two or more coloring agents. The solid phase additionally contains water-soluble active substances which are to be added to the preparation. The coloring agents are preferably inorganic and/or organic pigments, lakes, which are insoluble in water and/or in the above-mentioned lipid phase, of organic dyes and/or glitter agents based on coated mica, bismuth oxychloride, coated bismuth oxychloride, glass, flake-form metal powders which are at least partially coated with other materials, finely divided plastic flakes which are at least partially coated with other materials, preferably PET flakes or solid solutions of dyes in suitable plastic matrices, preferably in polyester-3. In quite general terms therefore the term pigments is used to denote white or colored, inorganic or organic particles which are insoluble in water and the respective medium and which are intended to color and/or cloud the composition. That can involve white or colored, inorganic and/or organic pigments of commercially available size of about between 0.1 and 200 µm or of particle sizes in the nanometer range, that is to say about between 5 and 100 nm, so-called "nanopigments". In particular aluminum oxide, titanium dioxide, zinc oxide and cerium oxide are to be named in that range. The choice of the coloring agents is preferably such that the use thereof and the amount employed correspond to the provisions of Enclosure 3 of the Cosmetic Regulations for Germany, which are based on the EC Directive applicable in respect of the European Union. Comparable regulations are also applicable in Japan and in the USA; suitable coloring agents are therefore preferably to be so selected that they preferably correspond world-wide to the respectively applicable regulations. Of the appropriate coloring agents mention will be made here by way of example of pigments such as titanium dioxide (C I No 77891), iron oxides (C I No 77491, 77492, 77499), ultra marine (C I No 77007), Berlin blue/Ferric blue (C I No 77510), carbon black (C I No 77267), chromium oxide green (C I No 77288), chromium hydroxide green (C I No 77289), manganese violet (C I No 77742), zinc oxide (C I No 77947), barium sulfate (C I No 77120), glitter agents such as for example mica, at least partially coated with titanium dioxide (C I No 77891) and/or with other metal oxides such as iron oxides, chromium oxide green or chromium hydroxide green or with ultramarine and the like coloring agents, bismuth oxychloride and mixtures thereof with mica (C I No 77163), at least partially coated with titanium dioxide and/or others of the aforementioned metal oxides or other coloring agents, flake-form, possibly finely divided metal powders such as for example aluminum (C I No 77000), copper (C I No 77400), bronze (C I No 77400), brass (C I No 77400), silver (C I No 77820) or gold (C I No 77480). Organic coloring agents are advantageously selected from the complex salts of carminic acid (C I No 75470) and/or coloring agents which were selected from fluoresceins, monoazo dyes, diazo dyes, indigotin dyes, pyrazol dyes, quinoline dyes, triphenyl methane dyes, anthraquinone dyes and xanthan dyes which are made insoluble in a suitable fashion by laking. Mentioned here by way of example are FD&C Red No 3 (C I No 45430), D&C Red No 6 (C I No 15850), D&C Red No 7 (C I No 15850:1), D&C Red No 21 (C I No 45380:2), D&C Red No 22 (C I No 45380), D&C Red 27 (C I No 45410:1), D&C Red 28 (C I No 45410), D&C Red 30 (C I No 73630), D&C Red No 33 (C I No 17200), D&C Red No 34 (C I No 15880:1), FD&C Yellow No 5, (C I No 19140), FD&C No 7 (C I No 45350:1), D&C Yellow No 10 (C I No 47005), D&C Orange No 5 (C I No 45370:1), D&C Orange No 10 (C I No 45425:1), FD&C Green No 3 (C I No 42053), D&C Green No 5 (C I No 61570), D&C Green No 6 (C I No 61565), FD&C Blue No 1 (C I No 42090), D&C Violet No 2 (C I No 60725). If those coloring agents are not used as insoluble lakes, they can also be used in the form of solid solutions in plastic materials. Such solid solutions are known and inexpensively commercially available, which intensively fluoresce under long-wave UV light, referred to as "black light", for example under the INCI names "Polyester-3, Red 22", "Polyester-3, Red 28", "Polyester-3, Yellow 10" or "Polyester-3, Blue 1", in which respect it is also possible to use mixtures of those solid solutions, possibly also with others of the above-mentioned coloring agents.

Depending on the desired effect and the nature of the desired product, the amount of the specified coloring agents used is between 0.1 and 50% by weight, preferably between 1 and 40% by weight and quite particularly preferably between 5 and 30% by weight. The amount used depends on the one hand on the color intensity of the pigment employed and on the other hand also on the later technology for manufacture of the desired product.

Water-soluble active substances are also added to the solid phase. A preferred water-soluble ingredient is a hyaluronic acid derivative or salt thereof. As stated hereinbefore the hyaluronic acid or the hyaluronic acid salt is added in the dried condition, possibly also in the form of microparticles, to the solids phase and distributed together with the solids phase in the lipid phase. After application the hyaluronic acid then serves to add water. The same effect, that is to say adding water, can also be achieved with other vegetable ingredients such as hydrolyzed wheat protein. The preparation according to the invention preferably contains at least one active substance which by absorbing water has a wrinkle-filling and skin-smoothing action.

Another preferred active substance which is contained in the solid phase is phytosphingosine or a derivative thereof, such as for example a phytosphingosine which is esterified with salicylic acid. Phytosphingosines and derivatives thereof stimulate collagen synthesis, which assists with skin regeneration and also has a smoothing effect.

A further water-soluble constituent which can be added to the solid phase, preferably in combination with phytosphingosines and/or hyaluronic acid salts are ceramides. Ceramides are frequently used in cosmetic compositions as they help to renew the natural protection layer of the skin and can form an effective barrier against loss of moisture. The combination of ceramides with hyaluronic acid derivatives and/or phytosphingosine derivatives is therefore particularly advantageous. Ceramide 3 is particularly preferably used as the ceramide.

Besides the above-mentioned ingredients the preparation according to the invention may also contain in the solid phase fillers such as for example talcum, kaolin, silicic acids, aluminum oxide which can possibly also be present in amorphous form, starch, modified starch, polytetrafluoroethylene powder ("Teflon"), polyamide powder, polyethylene powder, polypropylene powder and other polymer powders, boron nitride, insoluble metal soaps such as Mg stearate, Ca stearate, Sr stearate, Zn stearate and/or mixtures of those substances. Those finely divided or fibrous fillers which generally involve particle sizes of between 0.1 and 10 µm are used in amounts of between 0.1 and 25% by weight, preferably between 1 and 12% by weight. In addition it is also possible to use additives which are usual in cosmetics such as synthetic or natural fibers such as for example those comprising polyamides, polyesters, elastanes, polyacrylonitrile, rayon, viscose, artificial silk, silk, wool, cotton, linen, cellulose, cellulose regenerates or mixtures thereof, anti-oxidants, preserving agents, fragrances, anti-foam agents, thickening agents, dispersing additives, emollients, light protection agents for the purposes of product protection or as protection for the human body from the damaging effects of UV-A and UV-B radiation in sunlight and the like.

In a preferred embodiment the aforementioned preparation, in particular the cosmetic preparation, which, as already stated above, is present in the form of a lipid-based and water-free mixture, includes an also water-free combination of easily water-soluble active substances with lipid-based active substances and lipidic vegetable extracts in the form of an especially adapted active substance complex, that is to say what is referred to as a "vitalization complex" which is in the form of an "active substance cocktail" with vitalizing and energizing properties which counteract wrinkling and the visible signs of skin ageing. In that respect what has been found to be particularly suitable is a combination of water-soluble salts of vegetable extracts of which it is assumed that they have an action on the skin. The salts used are in particular salts of carboxylic acids with hydroxy functions, in particular di-, tri- and/or polyhydroxy acids with alkaline earth ions, zinc and/or copper ions. Salts of asparaginic acid and gluconic acid are particularly preferably used. Vegetable extracts which exert a beneficial action on the skin are known to the man skilled in the art. For example extracts of *Echium plantagineum* (viper's head) with *Cardiospermum halicacabum* (balloon vine) and *Helianthus annuus* (sunflower) have proven to be particularly suitable. The combination of *Echium plantagineum* (viper's head) with *Cardiospermum halicacabum* (balloon vine) and *Helianthus annuus* (sunflower) has a cell-regenerating, evening and harmonizing action and serves overall as very good skin protection.

The combination of magnesium aspartate, zinc gluconate and copper gluconate in that respect have an energizing and vitalizing effect and at the same time supply the skin with important trace elements. A combination of those three salts is therefore preferably used. Ascorbic acid derivatives are preferably used as radical catchers and anti-oxidants. Sodium ascorbyl phosphate is a form of vitamin C which is stable in respect of storage over a prolonged period of time—it acts as a radical catcher, it counteracts wrinkling and the visible signs of skin ageing and it promotes collagen synthesis in tissue and is therefore particularly preferably used. Of the hyaluronic acid derivatives sodium hyaluronate is a highly effective moisture provider and thus reduces wrinkle depth and has a regenerating action and is therefore also preferred. In combination the above-stated specific compounds lead to particularly advantageous effects.

A particularly preferred composition according to the invention therefore contains a combination of vegetable extracts of *Echium plantagineum, Cardiospermum halicacabum* and *Helianthus annuus* with magnesium aspartate, zinc gluconate and copper gluconate, sodium ascorbyl phosphate and sodium hyaluronic and with tocopheryl nicotinate. That leads to an active substance combination which exhibits an action which extends far beyond the action of the individual substance and which is surprising. Such an "active substance cocktail" exhibits a synergistic effect.

The amounts of the above-mentioned active substances used in the finished product, with respect to the total amount of the preparation, are between 0.01 and 1.5% by weight for magnesium aspartate and zinc gluconate, between 0.001 and 0.5% by weight for copper gluconate and sodium hyaluronate, between 0.1 and 10% by weight for sodium ascorbyl phosphate, between 0.01 and 2.0% by weight for tocopheryl nicotinate, niacin and niacin amide or mixtures thereof, and between 0.1 and 15% by weight for the lipidic combination of *Echium plantagineum* (viper's head) with *Cardiospermum halicacabum* (balloon vine) and *Helianthus annuus* (sunflower). Preferably extraction of the vegetable material is effected with a triglyceride such as sesame oil, rapeseed oil, sunflower oil or caprylic/capric triglyceride or with octyl dodecanol, hexyl oleate, jojoba oil or mixtures thereof. It is essential to the invention in that respect that the constituents in the active substance complex are also present in the intended amount in the ready-for-sale preparation—it is immaterial in that respect whether they are weighed out in individual portions and individually added to the mixture to be produced, or whether, to minimize errors and to improve the production procedure, two initial mixtures—a liquid phase which contains the lipid-soluble constituents and a solid phase which contains the water-soluble constituents in undissolved and therefore solid form—are produced. Experience has shown that, in terms of the finished end product, such a variation is of no significance.

A further particularly effective combination of ingredients is the following: phytosphingosine derivatives in combination with vegetal filling spheres and/or hyaluronic filling spheres which can possibly also be supplemented by tocopheryl nicotinate, D-panthenyl triacetate and/or ceramide 3.

It was found that tocopheryl nicotinate, D-panthenyl triacetate and ceramide 3 together with hyaluronic acid sodium salt form a particularly efficient active substance complex which smoothes and improves the appearance of the skin in a particular fashion.

Phytosphingosines stimulate collagen synthesis and thereby assist with skin renewal, they have a wrinkle smoothing action. Salicoyl phytosphingosine is particularly suitable as a phytosphingosine derivative. The phytosphingosine derivatives are preferably added in an amount of between 0.05 and 1% by weight, particularly preferably between 0.1 and 0.5% by weight, in each case with respect to the total composition.

In order to fill wrinkles and thereby achieve a skin smoothing effect it has proven to be advantageous to use swelling products in the form of balls. Microballs of natural polymers which are capable of swelling are particular suitable in that context. Hyaluronic acid and its derivatives and hydrolyzed wheat protein are particularly well suited to that purpose. In a particularly preferred embodiment those polymers are used in the form of balls which can comprise the polymer and optionally further inert carrier substances and can be coated or covered with a film in order to control properties such as swelling capability or also delivery capability. The products which are commercially available under the name "vegetal filling spheres" or "hyaluronic filling spheres" have proven to be particularly advantageous. Therefore vegetal filling spheres or hyaluronic filling spheres or a combination of both are particularly preferably added to the preparation according to the invention. The amount of those polymers used is in a range of between 0.5 and 10% by weight, preferably between 1.0 and 5% by weight, in each case with respect to the total preparation.

The esters of nicotinic acid have an action of promoting blood circulation—they can however certainly result in a hot flush which is perceived as being unpleasant, linked to intensive skin reddening. Esters such as ethyl nicotinate or benzyl nicotinate are also not distinguished by a particularly pleasant fragrance. In contrast a substantially milder effect is found with tocopheryl nicotinate which is also used as a radical catcher and anti-oxidant and preferably stimulates microcirculation in the upper layers of the skin—the same moreover also applies for niacin or niacin amide. in combination with phytosphingosines the nicotinate also contributes to a skin-smoothing action. In that combination it is preferably used in an amount of between 0.1 and 0.5% by weight with respect to the total preparation.

Panthenyl triacetate also promotes the action of the phytosphingosines and is therefore preferably used in combination therewith. The preferred amount is between 1 and 3% by weight with respect to the total preparation.

Ceramides promote cell regeneration and therefore also supplement the action of the phytosphingosines. They also supply moisture. They are preferably added in an amount of between 0.05 and 0.5, particularly preferably between 0.08 and 0.3% by weight, with respect to the total preparation.

A further ingredient which supplements the advantageous action is hyaluronic acid sodium salt which in that combination is preferably added in an amount of between 0.01 and 01% by weight with respect to the total preparation.

Overall a combination of phytosphingosine SLC, filling spheres, based on hydrolyzed wheat protein and/or hyaluronic acid or a salt thereof, tocopheryl nicotinate, D-panthenyl triacetate, ceramide 3 and hyaluronic acid sodium salt has proven to be a wrinkle-filling and smoothing active substance complex with very good properties and is therefore preferably used.

The preparation according to the invention can also be used as a workable cream or as a lead for a cosmetic pencil. The preparation is particularly well suited to the production of leads as the lead material is soft and delivers the preparation easily, but is nonetheless self-supporting.

A further advantage of the preparation according to the invention is that it is possible to produce leads with a high active substance content in the range of between 3 and 7, preferably between 3.5 and 5.5% by weight. Hitherto creams or ointments were produced as the active substance carrier; for leads, an active substance content as is now made possible by virtue of the specific composition was hitherto not considered to be appropriate. By virtue of the consistency which is produced by the combination of sold phase and lipid phase, it is therefore possible to produce novel textures in lead form.

The production of products in the form of pencils with a lead of a spreadable material can in that respect be effected using the basically known extrusion process in which the material is extruded under high pressure in the range of between and 100 MPa, preferably between 20 and 50 MPa, to form elongate portions which are then cut to length and introduced into a case of wood, wood substitutes or plastic material. It is also possible for a material which has been heated above its flow point to be cast into suitable molds—optionally with a point being formed thereon at the same time—, for the material to be allowed to cool therein and for the resulting moldings to be subjected to further processing after removal from the mold in accordance with the methods of the extrusion process. It is also possible for a material which has been heated above its flow point to be cast directly into suitable applicator devices.

The preparation according to the invention can be produced by a procedure whereby a preparation, in particular a cosmetic preparation, is firstly produced in conventional manner from a suitable lipid phase and a solids phase which is exactly the same, which preparation is suitable for the production of products in pencil or stick form or in the form of workable pastes which are suitable for cosmetic uses, in particular in the field of decorative cosmetics, for coloring, improving the appearance of and caring for keratinic materials such as for example the skin, semi-mucous membranes and mucous membranes, the lips and the eyelids and the surrounding area, and same is then provided with a combination of easily water-soluble and lipid-soluble active substances which can be present in the form of an active substance complex which is specifically adapted in respect of its action, in order to impart to the preparation according to the invention, besides decorative properties, pronounced caring qualities in the sense of ongoing vitalizing energizing effects which stimulate microcirculation and thus the skin substance transport action. Those effects are intended ultimately to positively influence the overall picture of the skin, improve the fine structure of the skin surface, reduce wrinkle depth and counteract fatigue phenomena and premature skin ageing. It will be appreciated in that respect that lipid-soluble active substances can be very easily incorporated into a lipidic phase. It was now surprisingly found that it is also possible for water-soluble and in particular easily water-soluble active substances to be well and uniformly incorporated into a lipidic phase—similarly to the above-mentioned solids phase in undissolved and therefore solid form—. In order however to liberate the water-soluble active substances therefrom again, moisture is required, which is present in the microclimate over the skin, in the form of perspiration or also water vapor. It is advantageous in that respect that the above-mentioned water-soluble active substances can in that way deploy a deposit effect as they are dissolved step by step out of the applied lipid film by virtue of the action of moisture. Accordingly they are available in an adequate amount over a prolonged period of time until the reserve is used up. By way of example mention may be made here of lipstick, lip rouge, blusher, lipliner, eyeliner, eyebrow pencils, hair coloring pencils, kohl, kajal, makeup pencils, masking pencils, concealer, effect party makeup, mascara, hair mascara, or eyeshadow. They can also be used—in unpigmented form or mixed with "non-coloring" so-called nanopigments—as lip care pencil, lip balm, lip gloss, as a fixing foundation for the lips, as a care foundation for care of the skin or as a sun protection agent.

In principle it is possible for a preparation and in particular a cosmetic preparation to be produced water-free and on a lipid basis, by a procedure whereby the lipid constituents are melted in a suitable vessel at elevated temperature, the solids phase is added by means of a high-speed agitator and that mixture is passed as required one or more times through a homogenizing device such as a three-roll mill, a corundum plate mill, a colloid mill (with heatable casing) or kneading apparatuses. The water-free "active substance cocktail" is incorporated into a part of the preparation and later homogenized with the main amount of the preparation. If the preparation includes glitter agents, they are only added prior to the last passage through the three-roll mill. The corundum plate mill or the colloid mill are prohibited in that specific case for homogenization of the preparation. The preparation obtained in that way is then extruded in the usual fashion to form elongate lines of pencil leads, which are cut to the required length and subjected to further processing to form cosmetic sticks or pencils in the manner known from the production of lead pencils, the cosmetic pencils having a casing produced in known manner of wood, wood substitute or a plastic material. Those pencils can be sharpened in conventional manner with a commercially available sharpener by shaving off their cases. The lead portions however can also be fitted into suitable rotary mechanisms as are known from DE 37 28 427 C2 or into transparent cases in accordance with EP 1 464 248 A1. It is also known however for such a preparation to be introduced into a suitable rotary mechanism at elevated temperature and in a liquid condition in accordance with EP 0 310 799 B1 or DE 44 45 230 C2 or 44 45 231 C2 or EP 1 150 588 B1 or U.S. Pat. No. 6,206,597. If such a preparation, in particular a cosmetic preparation, is produced in the form of a workable paste, it can also be filled for example into an applicator device in accordance with U.S. Pat. No. 6,238,117 or EP 1 426 118 A1 or EP 1 468 937 A1 or DE 20 2004 004 567 U1 and applied therefrom in a metered fashion as required. They can however also be filled into a tube or a bowl or a suitable pot of metal, at elevated temperature and in a liquid condition. If those products are produced in the form of a mascara or hair mascara then they are introduced in the usual manner into the containers which are intended for same and which are transparent or which are colored with the color of the material or the "corporate color" of the supplier and which have a removable closure cap with an applicator element fitted therein and secured to a carrier stem. Examples in that respect are described in EP 1 419 711 B1, EP 1 419 712 B1, EP 1 446 033 B1 and EP 1 463 425 B1.

The preparation according to the invention and in particular the cosmetic preparation will now be described in detail with reference to the Examples hereinafter which however do not definitively describe or limit it. In that respect the quantities are specified in percent by weight (% wt), in each case with respect to the total weight of the preparation, and the raw materials are identified with the "INCI names" which are generally known to the man skilled in the relevant art.

EXAMPLE 1

Vitalizing active substance complex

| Active substance complex lipid phase 1.1 | |
|---|---|
| Tocopheryl nicotinate | 10.000 |
| Octyl dodecanol + *Echium plantagineum* + *Cardiospermum halicacabum* + *Helianthus annuus* | 90.000 |
| Active substance complex solids phase 1.2 | |
| Magnesium aspartate | 8.000 |
| Zinc gluconate | 5.500 |
| Copper gluconate | 0.900 |
| Sodium ascorbyl phosphate | 81.100 |
| Sodium hyaluronate | 4.500 |

EXAMPLE 2

(Eyeliner)

| | | |
|---|---|---|
| (A) | Synthetic wax | 3.500 |
| | Polyethylene | 5.200 |
| | Polybutene | 4.800 |
| | Cera microcristallina | 1.600 |
| | Hydrogenated castor oil | 3.400 |
| | Buxus chinensis oil | 4.500 |
| | Phytosterols + Persea gratissima oil | 2.250 |
| | Theobroma grandiflorum | 2.20 |
| | Tetradibutyl pentaerythrityl hydroxyhydrocinnamate | 0.300 |
| (B) | Active substance complex lipid phase 1.1 | 6.750 |
| | Cyclopentasiloxane | 24.000 |
| | Dimethicone 1.5 cst | 11.500 |
| (C) | Silica silylate | 3.000 |
| | Ferric ferrocyanide (C I No 77510) | 9.700 |
| | Chromium hydroxide green (C I No 77289) | 4.300 |
| (D) | Active substance complex solids phase 1.2 | 6.000 |
| | Mica and titanium dioxide(C I No77891) | 7.000 |

For production of the preparation the constituents of phase (A) are introduced into a suitable vessel and by being heated they are melted until clear, then the constituents of phase (C) are dispersed therein with good agitation using a toothed ring agitator or the like. That mixture is now passed twice through a three-roll mill. The constituents of phase (D) are now distributed as uniformly as possible over the rolled material, the latter is thoroughly mixed once again and passed a further time through the mill. The mixture obtained is now melted once again with heating in a vacuum process installation, then the cyclopentasiloxane and the dimethicone and finally also the active substance complex lipid phase 1.2 are added. The mixture is briefly homogenized, deaerated and introduced into sealingly closing storage containers or prepared directly for hot filling into rotary mechanisms. The result obtained is a blue-green lead with a slight pearlescence, which can be applied to the edge of the lid very easily and uniformly, which adheres there firmly and for an extremely long period of time, which does not move from the place of application and which can be easily removed again with a commercially available makeup remover. Upon multiple application of that eyeliner the skin is stimulated in the sense of vitalization. The increase in microcirculation improves the substance transport effect, the fine structure of the skin surface by virtue of a reduction in wrinkle depth and smoothing of the fine wrinkling. The preparation thus counteracts premature skin ageing.

EXAMPLE 3

Eyeliner

| | | |
|---|---|---|
| (A) | Paraffin wax | 7.200 |
| | Hydrogenated castor oil | 4.500 |
| | Ozocerite | 4.300 |
| | PEG-6 beeswax | 3.600 |
| | Diisostearyl dimer dilinoleate | 6.250 |
| (B) | Active substance complex lipid phase 1.1 | 6.750 |
| | Cyclopentasiloxane | 30.300 |
| | Ascorbyl palmitate | 0.050 |
| | Tocopherol | 0.250 |
| | Methylparaben | 0.150 |
| | Propylparaben | 0.100 |
| | BHT | 0.050 |
| (C) | Iron oxide black (C I No 77499) | 2.700 |
| | Chromium oxide green (C I No 77288) | 14.000 |
| | Chromium hydroxide green (C I No 77289) | 4.200 |
| | Titanium dioxide (C I No 77891) | 2.600 |
| (D) | Mica and titanium dioxide (C I No 77891) | 7.000 |
| | Active substance complex solids phase 1.2 | 6.000 |

Production of the preparation and processing are effected in a similar manner to Example 2. The result obtained is a moss-green lead which can be produced by a casting process, which can be applied to the edge of the lid very easily and uniformly, which adheres there firmly and for an extremely long period of time, which does not move from the place of application and which can be easily removed again with a commercially available makeup remover. Upon multiple application of that eyeliner the skin is stimulated in the sense of vitalization. The increase in microcirculation improves the substance transport effect, the fine structure of the skin surface by virtue of a reduction in wrinkle depth and smoothing of the fine wrinkling. The preparation thus counteracts premature skin ageing.

EXAMPLE 4

Lipliner

| | | |
|---|---|---|
| (A) | Hydrogenated vegetable oil | 9.200 |
| | Hydrogenated castor oil | 3.900 |
| | Behenyl behenate | 4.500 |
| | Copernicia cerifera (carnauba) | 1.800 |
| | Buxus chinensis oil (jojoba oil) | 6.150 |
| | Butyrospermum parkii (shea butter) | 3.600 |
| | Behenic acid | 15.500 |
| (B) | Active substance complex lipid phase 1.1 | 5.800 |
| | Ascorbyl palmitate | 0.050 |
| | Tocopherol | 0.250 |
| | Methylparaben | 0.150 |
| | Propylparaben | 0.100 |
| (C) | Iron oxide yellow (C I No 77491) | 5.400 |
| | Iron oxide red (C I No 77492) | 24.200 |
| | Iron oxide black (C I No 77499) | 2.500 |
| | D&C Red 7 (C I No 15850:1) | 6.400 |
| | D&C Red 30 (C I No 73630) | 5.200 |
| (D) | Active substance complex solids phase 1.2 | 5.200 |

To produce the preparation the phase (A) is melted in a suitable vessel with heating until clear. The phase (C) is then homogenously incorporated with agitation with a toothed ring agitator. The mixture is now passed twice through a three-roll mill. The phase (B) is homogenally dissolved possibly with slight heating and distributed together with the phase (D) homogenously over the rolled material. The batch is then passed once again through a three-roll mill. The mass is now pressed to form an extrudable body and in that situation deaerated and then pressed under high pressure—at 40 to 60 MPa (400 to 600 bars)—to form elongate line portions which are cut to length and which are processed in known manner to form wood-encased pencils. The result obtained is a brown-red lead with good covering power, which can be well applied to the lip edges, which does not smear, which adheres for a long time, which does not transfer onto articles or other materials and which does not move away from the place of application into relatively fine skin wrinkles. Upon multiple application of that lipliner the skin is stimulated to afford a vitalization effect. The increase in microcirculation improves the substance transport effect, the fine structure of the skin surface by a reduction in wrinkle depth and smoothing of the fine wrinkling. The preparation thus counteracts premature skin ageing.

EXAMPLE 5

Lipliner

| | | |
|---|---|---|
| (A) | Polyethylene | 11.200 |
| | Cera alba (beeswax) | 3.250 |
| | Di-PPG-3 myristyl ether adipate | 3.100 |
| | Sucrose tetrastearate triacetate | 2.150 |
| | Pentaerythrityl tetrabehenate | 1.800 |
| | Isodecyl neopentanoate | 2.100 |
| | Dimethicone/vinyldimethicone crosspolymer | 1.700 |
| | Polybutene | 9.300 |
| | Trimethylsiloxysilicate | 6.300 |
| (B) | Cyclopentasiloxane | 28.000 |
| | Active substance complex lipid phase 1.1 | 4.500 |
| | Ascorbyl palmitate | 0.050 |
| | Tocopherol | 0.200 |
| | Methylparaben | 0.150 |
| | Propylparaben | 0.100 |
| (C) | Iron oxide red (C I No 77492) | 10.500 |
| | Iron oxide yellow (C I No 77491) | 1.300 |
| | Iron oxide black (C I No 77499) | 0.700 |
| | D&C Red 7 (C I No 15850:1) | 2.000 |
| | Stearalkonium bentonite | 0.300 |
| | Boron nitride | 3.300 |
| | Talcum | 4.000 |
| (D) | Active substance complex solids phase 1.2 | 4.000 |

To produce the preparation the constituents of phase (A) are melted with heating and agitation, in which respect care is to be taken to ensure that the trimethylsiloxysilicate dissolves completely in the lipid phase. The constituents of the solids phase (C) are then added and homogenously incorporated with agitation. The mixture is now passed twice through a three-roll mill. The phase (D) is now distributed over the rolled material as uniformly as possible, then the batch is passed once again through the mill and then melted once again with heating in a suitable vessel. In the meantime the constituents of the phase (B) are dissolved in the cyclopentasiloxane, thereafter the phase (B) is combined with the batch and well stirred thereinto. The mixture obtained is then cast into the above-described rotary mechanisms, using suitable apparatuses. The result obtained is a red lead with a slight brown tinge and with good covering power, which can be applied to the lip edges very well and uniformly, which does not smear, which adheres for a long time, which does not transfer onto articles or other materials and which does not move away from the place of application into relatively fine skin wrinkles. Upon multiple application of that lipliner the skin is stimulated to afford a vitalization effect. The increase in microcirculation improves the substance transport effect, the fine structure of the skin surface by a reduction in wrinkle depth and smoothing of the fine wrinkling. The preparation thus counteracts premature skin ageing.

EXAMPLE 6

Lip Gloss in Cream Form

| | | |
|---|---|---|
| (A) | Polybutene | 17.600 |
| | Behenyl behenate | 3.300 |
| | Copernicia cerifera (carnauba) | 3.700 |
| | Isostearyl isostearate | 3.000 |
| | Dimethicone 200 cst | 4.400 |
| | Phenyltrimethicone | 1.300 |
| | Trimethylsiloxysilicate | 5.500 |
| (B) | Isododecane | 10.000 |
| | Cyclopentasiloxane | 23.500 |
| | Active substance complex lipid phase 1.1 | 5.200 |
| | Phenoxyethanol | 0.400 |
| | Ascorbyl palmitate | 0.050 |
| | Tocopherol | 0.200 |
| | Methylparaben | 0.150 |
| | Propylparaben | 0.100 |
| (C) | Mica and titanium dioxide (C I No 77891) | 14.000 |
| | D&C Red 7 (C I No 15850:1) | 2.600 |
| (D) | Active substance complex solids phase 1.2 | 5.000 |

To produce the preparation the constituents of phase (A) are melted with heating and agitation in a suitable vessel, in which respect care is to be taken to ensure that the trimethylsiloxysilicate dissolves completely in the lipid phase. Approximately a quarter of that lipid phase is now taken off and the D&C Red 7 is stirred therein. That mixture is passed twice through a three-roll mill. The phase (D) is now scattered as uniformly as possible onto the rolled material, thoroughly mixed and that amount is passed once again through a three-roll mill and the rolled material is combined with the melted remainder of the phase (A). The pearlescent pigment is now scattered into the material, with good agitation. In the meantime all constituents of the phase (B) were dissolved in the isododecane. The cyclopentasiloxane is now added and the phase (B) is added to the mixture with agitation. The mixture is now cooled with slight agitation to about 35-40° C. in order to prevent settlement of the coloring agents and the material is transferred into sealingly closing storage containers in order for them to be later filled for example into application devices in accordance with U.S. Pat. No. 6,238,117 or EP 1 426 118 A1 and applied therefrom. The result obtained is a creamy, strongly shiny lip gloss which can be applied very easily and uniformly and also—with the above-stated devices—also with a sharp contour to the skin of the lips and which remains adhering there for a long time and which does not move away from the place of application. Upon multiple application of that lip gloss the skin is stimulated to afford a vitalization effect. The increase in microcirculation improves the substance transport effect, the fine structure of the skin surface by a reduction in wrinkle depth and smoothing of the fine wrinkling. The preparation thus counteracts premature skin ageing.

EXAMPLE 7

Lip Care Pencil with Light Protection

| | | |
|---|---|---|
| (A) | Acetylated lanolin | 7.500 |
| | Lanolin | 17.700 |
| | Cera alba(beeswax) | 10.000 |
| | Behenyl behenate | 7.300 |
| | Copernicia cerifera (carnauba) | 1.800 |
| | Castor oil | 24.300 |
| (B) | Isododecane | 10.000 |
| | Active substance complex lipid phase 1.1 | 5.200 |
| | Ascorbyl palmitate | 0.050 |
| | Tocopherol | 0.200 |
| | Methylparaben | 0.150 |
| | Propylparaben | 0.100 |
| (C) | Titanium dioxide (C I No 77891) - nanopigment | 7.500 |
| | Mica and titanium dioxide (C I No 77891) | 2.500 |
| | Iron oxide red (C I No 77491) | 0.500 |
| | D&C Red 7(C I No 15850:1) | 0.200 |
| (D) | Active substance complex solids phase 1.2 | 5.000 |

To produce the preparation the phase (A) is melted in a suitable vessel. Approximately a quarter thereof is removed, the coloring agents of phase (C) with the exception of the pearlescent agent are mixed therein and passed twice through a three-roll mill. The phase (D) and the pearlescent pigment are now scattered over the rolled material as uniformly as possible and it is passed once again by way of a three-roll mill. In the meantime the constituents of the phase (B) have been dissolved in the isodecane. The rolled material is now combined with the remainder of the phase (A) and the homogenous mixture is added to the phase (B). The finished mixture is introduced into sealingly closing storage containers or passed directly for further processing. The material is preferably suitable for filling into known spindle-type mechanisms; it can however also be processed in the manner usual in relation to lipstick production to form pencil lead castings which are fitted into suitable rotary mechanisms by machine or manually. Upon multiple application of that lip care pencil the skin is stimulated to afford a vitalization effect. The increase in microcirculation improves the substance transport effect, the fine structure of the skin surface by a reduction in wrinkle depth and smoothing of the fine wrinkling. The preparation thus counteracts premature skin ageing.

EXAMPLE 8 Anti-wrinkle, line-filling and hydrating active substance complex

| | |
|---|---|
| Active substance complex lipid phase 1.1 | 5.500 |
| Tocopheryl nicotinate | |
| Pentaerythrityl tetraisostearate + Silica dimethyl silylate + Hydrolyzed wheat protein | 44.000 |
| Panthenyl triacetate | 50.500 |
| Active substance complex solids phase 1.2 | 15.000 |
| Sodium hyaluronate | |
| Salicyloyl phytosphingosine | 55.000 |
| Ceramide 3 | 30.000 |
| Active substance complex lipid phase 1.3 | 5.500 |
| Tocopheryl nicotinate | |
| Ethylhexyl palmitate + silica dimethyl silylate + butylene glycol + sodium hyaluronate | 44.000 |
| Panthenyl triacetate | 50.500 |

A lipid phase and a solids phase are respectively produced from the specified ingredients. For the following products, a lipid phase and the solids phase are respectively combined. Cosmetic products with a skin-smoothing action are obtained.

EXAMPLE 9

Lipliner

| | | |
|---|---|---|
| (A) | Synthetic wax | 2.000 |
| | Hydrogenated stearyl olive esters | 2.500 |
| | Synthetic beeswax | 4.800 |
| | Hydrogenated jojoba oil | 3.700 |
| | Candelilla cera | 8.000 |
| | Copernicia cerifera (carnauba) | 6.000 |
| | Bis-diglyceryl polyacyladipate-2 | 7.500 |
| | Coco-caprylate/caprate | 2.500 |
| | Tetradibutyl pentaerythrityl hydroxyhydrocinnamate | 0.300 |
| (B) | Active substance complex lipid phase 1.1 | 4.700 |
| | Cyclopentasiloxane | 35.000 |
| | Octyldodecanol | 2.000 |
| (C) | Silica silylate | 5.000 |
| | Iron oxide red (C I No 77492) | 6.800 |
| | Iron oxide black (C I No 77499) | 0.800 |
| | D&C Red 7 (C I No 15850:1) | 2.100 |
| (D) | Mica and titanium dioxide (C I No 77891) | 4.300 |
| | Active substance complex solids phase 1.2 | 2.000 |

The ingredients were processed as described in Example 2. The resulting preparation was used to produce a lipliner which could be easily applied, which was perceived as being pleasant, which had a skin-hydrating action, which filled wrinkles and which visually smoothed the skin. That lipliner can be used as an "anti-wrinkle" product.

EXAMPLE 10

Hydrated lipstick

| | | |
|---|---|---|
| (A) | Polybutene | 13.000 |
| | Polyethylene | 7.000 |
| | Cera microcristallina | 5.000 |
| | Isopropyl myristate | 29.000 |
| | Pentaerythrityl tetraisostearate | 18.200 |
| | Cetearyl behenate | 3.000 |
| | Polyglyceryl-2 dipolyhydroxystearate | 1.900 |
| (B) | Active substance complex lipid phase 1.1 | 4.700 |
| | Tocopherol | 0.200 |
| | Ascorbyl palmitate | 0.050 |
| (C) | Titanium dioxide (C I No 77891) - nanopigment | 5.400 |
| | D&C Red 7 (C I No 15850:1) | 0.950 |
| | Iron oxide yellow (C I No 77491) | 0.700 |
| | Iron oxide red (C I No 77492) | 2.000 |
| (D) | Mica and titanium dioxide (C I No 77891) | 6.900 |
| | Active substance complex solids phase 1.2 | 2.000 |

The ingredients are processed with a method as described in Example 2 to provide a preparation which is formed into a lipstick. The lipstick produces a pleasant feeling on the skin.

EXAMPLE 11

Eyeliner

| | | |
|---|---|---|
| (A) | Paraffin wax | 8.000 |
| | Ozokerite | 4.000 |
| | Hydrogenated jojoba oil | 6.100 |
| | Pentaerythrityl tetraisostearate | 14.000 |
| | Isopropyl palmitate | 7.500 |
| (B) | Active substance complex lipid phase 1.1 | 4.700 |
| | Cyclopentasiloxane | 32.000 |
| | Tocopherol | 0.200 |
| | Ascorbyl palmitate | 0.050 |
| (C) | Iron oxide yellow (C I No 77491) | 4.000 |
| | Iron oxide black (C I No 77499) | 5.500 |
| | Ferric ferrocyanide (C I No 77510) | 9.950 |
| (D) | Mica and titanium dioxide (C I No 77891) | 2.000 |
| | Active substance complex solids phase 1.2 | 2.000 |

A method as described in Example 2 is used to process the ingredients to afford a preparation which is used as an eyeliner. The eyeliner can be applied well, it has a smoothing action and it supplies the skin with moisture.

EXAMPLE 12

Lipliner

| | | |
|---|---|---|
| (A) | Hydrogenated stearyl olive esters | 3.000 |
| | Synthetic beeswax | 4.800 |
| | Hydrogenated jojoba oil | 6.700 |
| | Candelilla cera | 9.000 |
| | Copernicia cerifera (carnauba) | 5.000 |
| | Bis-diglyceryl polyacyladipate-2 | 7.500 |
| | Tetradibutyl pentaerythrityl hydroxyhydrocinnamate | 0.300 |
| (B) | Active substance complex lipid phase 1.3 | 4.700 |
| | Cyclopentasiloxane | 34.000 |
| | Octyldodecanol | 4.000 |
| (C) | Silica silylate | 5.000 |
| | Iron oxide yellow (C I No 77491) | 4.700 |
| | Iron oxide black (C I No 77499) | 0.800 |
| | D&C Red 30 (C I No 73630) | 1.900 |
| (D) | Active substance complex solids phase 1.2 | 2.000 |
| | Mica and titanium dioxide (C I No 77891) | 6.600 |

A method as described in Example 2 is used to process the ingredients to afford a preparation which is used as lipliner. Application is long-lasting and provides an anti-wrinkle effect.

EXAMPLE 13

Lipstick

| | | |
|---|---|---|
| (A) | Polyethylene | 3.000 |
| | Cera alba (beeswax) | 10.000 |
| | Candelilla cera | 8.000 |
| | Octyldodecanol | 5.000 |
| | Pentaerythrityl tetraisostearate | 16.700 |
| | Cetearyl behenate | 2.000 |
| | Tetrabutyl pentaerythrityl hydroxyhydrocinnamate | 0.200 |

-continued

| | | |
|---|---|---|
| (B) | Active substance complex lipid phase 1.3 | 4.700 |
| | Isododecane | 18.000 |
| (C) | Titanium dioxide (C I No 77891) - nanopigment | 6.400 |
| | D&C Red 30 (C I No 73630) | 1.300 |
| | Iron oxide black (C I No 77499) | 0.500 |
| | Iron oxide red (C I No 77492) | 7.200 |
| (D) | Mica and titanium dioxide (C I No 77891) | 15.000 |
| | Active substance complex solids phase 1.2 | 2.000 |

As stated in Example 2 the ingredients are processed to afford a preparation which is formed into a lipstick. The lipstick is found to be very pleasant due to its hydrating action.

The invention claimed is:

1. Water-free preparation for application to the skin comprising a lipid phase with a solid phase distributed therein and an active substance system, wherein the active substance system is a combination of water-soluble and lipid-soluble active substances, wherein the water-soluble active substances are present in the solid phase while the lipid-soluble active substances are present dissolved in the lipid phase, and wherein the water-soluble active substances are those whose solubility is at least 10 g per 100 g of water.

2. A preparation as set forth in claim 1, comprising a decorative cosmetic, for coloring, improving the appearance of and caring for keratinic materials selected from the group consisting of the skin, semi-mucous membranes and mucous membranes, the lips, the eyelids, the eyelashes and the eyebrows.

3. A preparation as set forth in claim 1, wherein the preparation is in the form of a workable paste.

4. A preparation as set forth in claim 1, wherein the preparation is in the form of a lead which can be fitted into a pencil.

5. A preparation as set forth in one of claims 3 and 4, wherein oil, fat and waxes are used in proportions that a workable material is produced.

6. A preparation as set forth in claim 1, wherein the active substance system contains hyaluronic acid or a hyaluronic acid salt or hyaluronic acid derivative.

7. A preparation as set forth in claim 1, wherein the solid phase contains hyaluronic acid or a hyaluronic acid derivative, phytosphingosine or a phytosphingosine derivative and/or at least one ceramide.

8. A preparation as set forth in claim 1, wherein the lipid phase contains at least one vitamin or vitamin derivative.

9. A preparation as set forth in claim 1, wherein the lipid phase contains tocopheryl nicotinate and/or panthenyl triacetate.

10. A preparation as set forth in claim 1, wherein the lipid phase contains hydrolyzed wheat protein.

11. A preparation as set forth in claim 1, wherein the solid phase contains an alkaline earth, zinc and/or copper salt of a hydroxy group-bearing acid.

12. A preparation as set forth in claim 1, wherein the solid phase contains a combination of magnesium aspartate, zinc gluconate, copper gluconate, sodium ascorbyl phosphate and sodium hyaluronate.

13. A preparation as set forth in claim 1, wherein the lipid phase contains a combination of vegetable extracts.

14. A preparation as set forth in claim 13, wherein the lipid phase contains a combination of extracts of *Echium plantagineum, Cardiospermum halicacabum* and *Helianthus annuus*.

15. A preparation as set forth in claim 1, wherein the active substance system comprises a combination of phytosphingosine, hyaluronic acid or a derivative thereof and/or hydrolyzed wheat protein, tocopheryl nicotinate, D-panthenyl triacetate, ceramide 3 and hyaluronic acid sodium salt.

16. A preparation as set forth in claim 15, wherein the active substance system comprises hyaluronic acid and/or wheat protein in the form of microparticles which can be coated.

17. A preparation as set forth in claim 1, wherein the lipid phase is selected from the group consisting of fats, oils, oil-soluble vegetable extracts, saturated straight and/or branched-chain alcohols with chain lengths of between $C_3$ and $C_{40}$, saturated straight and/or branched-chain medium- to long-chain fatty acids with chain lengths between $C_6$ and $C_{40}$, or those with at least one double bond and/or their esters and/or waxes and mixtures thereof.

18. A preparation as set forth in claim 1, wherein the lipid components which are liquid at ambient temperature are used in the range of between 5 and 80% by weight.

19. A preparation as set forth in claim 1, wherein the lipid components which are liquid at ambient temperature are used in the range of between 15 and 50% by weight.

20. A preparation as set forth in claim 1, wherein the lipid components which are solid at ambient temperature are used in the range of between 1 and 65% by weight.

21. A preparation as set forth in claim 1, wherein the lipid components which are solid at ambient temperature are used in the range of between 5 and 45% by weight.

22. A preparation as set forth in claim 1, wherein the solid phase comprises finely divided fillers and at least one coloring agent or mixtures thereof.

23. A preparation as set forth in claim 1, wherein finely divided fillers of the solid phase are selected from the group consisting of talcum, kaolin, starch, modified starch, polytetrafluoroethylene powder ("Teflon"), polyamide powder, polyethylene powder, polypropylene powder and other polymer powders, boron nitride, insoluble metal soaps such as Mg stearate, Ca stearate, Sr stearate, Zn stearate and mixtures thereof.

24. A preparation as set forth in claim 1, further comprising additives selected from the group consisting of synthetic or natural fibers such as for example those of polyamides, polyesters, elastanes, polyacrylonitrile, rayon, viscose, artificial silk, silk, wool, cotton, linen, cellulose, cellulose regenerated and mixtures thereof, anti-oxidants, preserving agents, fragrances, anti-foam agents, thickening agents, dispersing additives, emollients, light protection agents and mixtures thereof.

25. A preparation as set forth in claim 1, wherein coloring agents of the solids phase are selected from the group consisting of inorganic and/or organic pigments, lakes which are insoluble in water or the lipid phase of organic dyes and/or glitter agents based on coated mica, bismuth oxychloride, coated bismuth oxychloride, glass, flake-form metal powders at least partially coated with other materials, finely divided plastic flakes at least partially coated with other materials, preferably PET flakes or solid solutions of dyes in suitable plastic matrices, preferably in polyester-3 and mixtures thereof.

26. A preparation as set forth in claim 25, wherein the solid solutions of dyes in polyester-3 are solid solutions which fluoresce intensively in long-wave UV light.

27. A preparation as set forth in claim 26, wherein said solid solutions which fluoresce intensively in long-wave UV light were selected from "Polyester-3, Red 22", "Polyester-3, Red 28", "Polyester-3, Yellow 10" or "Polyester-3, Blue 1", in the form of mixtures with others of the above-mentioned coloring agents.

28. A preparation as set forth in claim 25, wherein the coloring agents are used in an amount of between 0.1 and 45% by weight.

29. A preparation as set forth in claim 25, wherein the coloring agents are used in an amount of between 1 and 40% by weight.

30. A preparation as set forth in claim 25, wherein the coloring agents are used in an amount of 5 and 30% by weight.

31. A preparation as set forth in claim 23, wherein the finely divider fillers of the solids phase are used in an amount of between 0.1 and 25% by weight.

32. A preparation as set forth in claim 23, wherein the finely divider fillers of the solids phase are used in an amount of between 1 and 12% by weight.

33. A preparation as set forth in claim 1, wherein the preparation is in the form of a cast lead, wherein the preparation was poured into suitable molds at a temperature above its flow point and was cooled therein.

34. A preparation as set forth in claim 1, wherein the preparation is in the form of one of a lipstick, lipliner, eyeliner, eyeshadow, kohl, kajal, eyebrow pencil, masking pencil (so-called "concealer"), blusher, makeup pencil or hair coloring pencil.

35. A preparation as set forth in claim 1, wherein the preparation is in the form of a workable paste as lip rouge, blusher, makeup, effect party makeup, mascara, hair mascara, concealer or eyeshadow.

36. A preparation as set forth in claim 14, wherein the preparation is an eyeliner.

37. A preparation as set forth in claim 15, wherein the preparation is a lipliner.

* * * * *